United States Patent [19]

Ginaven et al.

[11] Patent Number: 5,457,041
[45] Date of Patent: Oct. 10, 1995

[54] NEEDLE ARRAY AND METHOD OF INTRODUCING BIOLOGICAL SUBSTANCES INTO LIVING CELLS USING THE NEEDLE ARRAY

[75] Inventors: Robert O. Ginaven, Encinitas; Daniel Facciotti, Davis, both of Calif.

[73] Assignee: Science Applications International Corporation, San Diego, Calif.

[21] Appl. No.: 218,059

[22] Filed: Mar. 25, 1994

[51] Int. Cl.$^6$ .................... C12N 5/10; C12M 1/00
[52] U.S. Cl. .................... 435/172.1; 435/285.1; 935/53; 935/85
[58] Field of Search .................... 435/172.1, 172.3, 435/287, 292, 293; 935/52, 53, 85; 422/100

[56] References Cited

U.S. PATENT DOCUMENTS 5,262,128  11/1993  Leighton et al. .................... 422/100

FOREIGN PATENT DOCUMENTS

0292899  11/1988  European Pat. Off. .................... 435/287

Primary Examiner—William H. Beisner
Attorney, Agent, or Firm—Fitch, Even, Tabin & Flannery

[57] ABSTRACT

An array of micro-needles extending from a support substrate and having tip portions shaped and dimensioned to (1) carry a biological substance and (2) pierce the surface of a target tissue and penetrate target cells within the tissue where the biological substance transfers from the tip portions and deposits within the target cells.

18 Claims, 5 Drawing Sheets

NEEDLE ARRAY AND METHOD OF INTRODUCING BIOLOGICAL SUBSTANCES INTO LIVING CELLS USING THE NEEDLE ARRAY

FIELD OF INVENTION

The present invention relates to improved apparatus and methods for introducing biological substances into living plant and animal cells, and, more particularly, to a needle array for carrying a biological substance and to a method of using the needle array to introduce the biological substance carried thereby into such living cells. As used herein, "biological substances" includes, by way of example, DNA, RNA, proteins, nuclei, organelles, vesicles, hormones, metabolites and infectious agents including bacteria, virus, viral particles and virions.

BACKGROUND OF THE INVENTION

Expression of heterologous nucleic acids in various biological systems is a necessary tool in the study of gene regulation as well as a powerful technique in the development of agricultural varieties of plants, algae, fungi, and animals which possess improved traits. DNA or RNA may be introduced, for instance, into cells for transient gene expression wherein the introduced nucleic acids remain episomal and are not integrated into the replicating genetic material of the host cell. Transient expression of heterologous nucleic acids is valuable for testing the functional level of regulatory sequences in directing native RNA polymerases to precisely transcribe the gene of interest and polyadenylate the RNA transcript. Transient gene expression is also valuable to test the level and fidelity of sense or antisense transcription, translation and ultimately the functionality of the heterologous gene product.

Transgenic organisms, on the other hand, comprise plants and animals that have heterologous nucleic acid sequences artificially integrated as functional addendum to their natural genetic repertoire. Transgenic organisms also comprise plants and animals that have antisense heterologous nucleic acids integrated into their genetic repertoire to effect the attenuation of natural or artificial gene expression. See, e.g., U.S. Pat. No. 5,175,385 to Wagner et al.; U.S. Pat. No. 5,185,384 to Krimpenfort et al.; U.S. Pat. No. 5,175,383 to Leder et al.; U.S. Pat. No. 4,736,866 to Leder et al.; and U.S. Pat. No. 5,107,065 *Anti-Sense Regulation of Gene Expression in Plant Cells*. A successfully produced transgenic organism permanently contains the heterologous nucleic acid sequence stably integrated in a non-deleterious manner into its native genetic composition and is able to pass the corollary trait on to its natural progeny. Techniques are needed for efficient transformation of single cells, cells comprising tissues, and the production of transgenic organisms.

Functional nucleic acid sequences are introduced into living cells in various ways including well known methods using calcium phosphate and DEAE-dextran and polybrene mediated transfection, protoplast fusion, and introduction via cationic liposomes. Cells and tissues from different sources contrast sharply in their ability to take up and express exogenously added DNA and RNA. Irrespective of the method used to introduce nucleic acids into eucaryotic and procaryotic cells, the efficiency of transient or stable transformation and gene expression is determined largely by the cell and tissue type that is used.

The innate ability of the natural plant pathogen *Agrobacterium tumefaciens* to incorporate its own DNA into certain plant genomes has been widely utilized to transfer foreign genes into plants by artificial engineering of the natural transferred portion of the pathogen plasmid DNA. Agrobacterium-mediated plant cell transformation has been found to be successful in a limited number of dicot plants including tobacco, petunia and carrot. Unfortunately, important agronomic monocotyledonous crops such as wheat, asparagus, barley, rye, corn and canola are generally not susceptible to transformation by *Agrobacterium tumefaciens*. The production of transgenic plants via *Agrobacterium tumefaciens* is further limited by the applicability of this method to species where one or a few transformed cells, e.g. leaf cells, can be regenerated into whole plants by means of artificial hormonal stimuli. Methods exist for regeneration of relatively few agronomic dicots and are virtually non-existent for monocots.

Methods used for transformation of plant cells also include electroporation and microinjection. To transform living cells by electropotation, cells are subjected to an electric shock to cause those cells to uptake DNA from surrounding fluid. Although protoplasts from such monocotyledonous plants as corn and rice have been successfully transformed by electroporation, current methods for the regeneration of whole monocot crop plants are limited to certain varieties. The need for genetic transformation of corn and wheat as well as many other agronomically important crops exists due to the potential to improve their disease resistance and output traits.

Methods of microinjection are described in U.S. Pat. No. 5,255,750, *Microinjection Apparatus and Method of Controlling Microinjection*; U.S. Pat. No. 5,114,854 *Process of Effecting a Microinjection Into Living Cells*; and U.S. Pat. No. 4,743,548 *Plant Cell Microinjection Technique*. Microinjection is a tedious process that requires microscopic manipulation of single cells (usually very large cells such as oocytes and plant cells without cell walls) and therefore is not practical for gene implant into plant tissues.

One modification of microinjection involves pricking the cell nuclei with a solid glass needle to allow biological solutions to enter which surround the cell (Yamamoto, M. et al., Exp. Cell Res., 142:79–84 (1982)). The pricking of single cell nuclei has at least the same limitations as microinjection and has only been demonstrated in mouse fibroblast nuclei.

U.S. Pat. No. 2,309,391, *A Device for Injectively Treating Plants*, describes a method of macro-injection wherein a large hand-held device artificially fertilizes or infects large plants, such as trees, by means of injection of fluids through hollow needles.

More recently, plant tissue transformation has been produced through the use of particle-mediated "gene gun" technology. See, e.g. Sanford, *The Biolistic Process TIB-TECH*, 6:299–302 (1988); and U.S. Pat. No. 5,204,253 *Method and Apparatus for Introducing Biological Substances into Living Cells*. According to such "gene gun" technology, DNA or RNA is coated on micro spherical carrier particles of a dense metal, e.g., tungsten, gold or platinum. The carrier particles are accelerated to physically pierce and imbed within a living target tissue to carry nucleic acid into the tissue. A number of different mechanisms have been employed to accelerate and project the coated carrier particles into target tissue including gunpowder ignition, pressured gas and a shock wave created by electric shock.

In practice, it has been difficult to accurately control the delivery and distribution of the coated carrier particles using such particle accelerating mechanisms. This has usually resulted in highly inefficient transformation of the desired microscopic growth regions in target tissues. For example, the distribution pattern of the micro particles often comprise a spaced pattern of dense clusters of coated particles in the target tissue accompanied by multiple particle entries per cell which often have deleterious or lethal physical effects upon the target cells and tissue. In other instances, the distribution pattern of coated particles may be too sparse to produce any useful cell transformations in a particularly valuable target tissue such as a meristem tissue of a plant, even after many attempts at site specific impregnation in the target tissue. Further, "gene gun" methods presently call for use of a vacuum (which can damage tissue by expansion or desiccation), and are implemented with expensive and complex systems and apparatus requiring complex calculations, settings, configurations and experimentation in order to operate the systems with any degree of success using various biological tissues.

Therefore, there is a continuing need for a relatively simple and inexpensive instrument and method for precisely controlled site-specific delivery of biological substances to the cytoplasm of a wide variety of tissue cells in situ. The present invention satisfies that need.

SUMMARY OF THE INVENTION

Basically, the apparatus of the present invention comprises an array of micro-needles substantially normal to and extending from a substrate or support base. The needles carry a biological substance or micro-particles coated with a biological substance for implantation into target cells within a living target tissue. To accomplish such implantation according to the basic method of the present invention, the target tissue is secured relative to the needle array. The needles of the array are shaped and dimensioned such that upon a pressing of the array of needles against an outer surface of the target tissue, the needle tips pierce the surface of the target tissue. Continued pressing on the needle array causes the needles to penetrate the target tissue until the tip portions pierce and extend into the target cells to transfer the biological substance to the target cells.

The needle array may be fashioned from any functional non-toxic substance most preferably but not limited to silicon, glass, ceramic, carbon, diamond, sapphire and the like and may be coated with any non-toxic functional substance including but not limited to polytetrafluoroethylene (Teflon®), silicon, latex, polystyrene, hydroxyapatite, gold, platinum and the like. A preferred embodiment comprises a structural array of micro-needles formed from a silicon wafer by means of photo lithographic etching.

An important feature of the needle array of the present invention is the capability of matching the array geometry to the target tissue. In general, the individual needles should be as thick as possible for strength, biological substance holding capacity and ease of low cost fabrication. However, the needles must be thin enough to penetrate the target cells without excessively damaging the target tissue.

Also, the spacing of the needles should be chosen to provide as many needle tips as possible within a target area for the array while avoiding excessive tissue damage by multiple penetrations of the same target cell. Needle spacings substantially equal to the width of the target cells avoid or substantially minimize such problems. Moreover, the needle array may be sized to correspond substantially in width and length to the size of the target area and thereby avoid needle contact of areas other than the target area.

The length of the needles should be chosen to carry and deposit biological substances at appropriate depths within the target cells. Needles having a length sufficient to place their tips about the middle of the target cells are appropriate. Thus, needle length and inter spacing dimensions of the needle array may be varied to accommodate optimal delivery of biological substances to individual target cells of different tissues.

In the later regard, the tips of the needles preferably are shaped to efficiently carry biological substances, or microparticles covered with biological substances, for transfer into the target cells. This may be accomplished by pointed or flat tips coated with or carrying the biological substances or by hollowed or concave tips for holding the biological substances or micro-particles coated with the biological substances. An optimal tip configuration may comprise a cage-like or ragged tip with an array of sharp protrusions such as a central or major peak surrounded by side or minor peaks. Such a configuration includes sharp peaks for piercing the surface of the target tissue, interspersed with nooks and crannies for releasably holding and carrying the biological substances.

As in conventional "gene gun" technology where microparticles are coated with biological substances, biological substances such as RNA and DNA may be deposited onto the needle array in a variety of ways including precipitation of the nucleic acid directly onto the structures, or by "dipping" in a non-toxic nucleic acid carrier suspension, for example a viscous substance such as glycerol or aqueous poly ethylene glycol, prior to delivery. The embodiment of the present invention comprising a cage-like structure at the needle tips provides enhanced carrying capabilities for holding of biological substances as well as capillary action for holding solutions or micro-particles coated with a biological substance for delivery to cell interiors.

Preferred dimensions for the needle array include but are not limited to needle lengths from between about 10 to about 25 μm, needle diameters from between about 0.5 to about 3 μm, inter-spacing of between about 5 to about 20 μm between the longitudinal axis of each needle in a linear array, and an array size up to about 20 by 20 needles.

In the method of delivery of biological substances using the needle array described herein, it is preferred that cell membrane perforations remain open for only a fraction of a second in order to minimize damage to the integrity of the cells comprising, for instance, meristem tissue. Natural lipid bilayer plasma membranes tend to reseal following minor non-traumatic disruption. Therefore a very rapid linear motion is preferred to effect puncture and withdrawal of the tip portions of the needle array from the cell during delivery of biological materials contained on the needle tips or on micro-particles carried by the needle tips. Nucleic acids DNA and RNA are extremely soluble in aqueous solutions such as the cytoplasmic contents of a living cell. Therefore, nucleic acids contained on the needle tips of the array or on the micro-particles carried by the needle tips quickly solubilize in the cell cytosol and trade adherence from the needle tips and micro-particles to the cytoplasm upon rapid linear withdrawal of the needle array. Alternatively, it may be desired to leave tips of the needles coated with the biological substances in the target cells for extended periods or even permanently. In such instances, at least the tip ends of the needles may be broken off immediately after insertion into the target cells as by the application of ultrasonic energy to, or lateral movement of, the needles followed by a rapid withdrawal of the balance of the needles from the cells. Further, such breaking of the needles may be enhanced by fabricating the needles with break away tip ends. Alternatively, the needles may be fabricated with detachable or releasably supported tip ends.

In the method of the present invention, target cells can be somatic cells of plant, animal, fish or any other life form or they can be germ line cells of the organism. Thus, the apparatus and method of the present invention appear suited for application to human treatment, where somatic cell transformation is viewed as a potential route for treatment of genetic diseases. Also, any animal, fish, or plant tissue may be employed in accordance with the present invention, including but not limited to angiosperms, gymnosperms, monocotyledons, and dicotyledons.

Further, gene implantation using the needle array apparatus and method of the present invention may be preferably performed in plant developing tissues including, but not limited to: meristem, embryo, leaves, shoots, roots, cotyledons, shoot apex, scutellum, epicotyl, hypocotyl, stamens, receptacle, anthers, stigma, ovary, carpel, endosperm and seed germ. Still further, transgenic plants resulting from impregnation of genic constructs with the apparatus and method of the present invention, for instance meristem tissue cells, may be selected for in the second or later generations.

Plants of interest include cereals such as wheat, barley, maize, triticale, etc.; fruits, such as apricots, oranges, grapefruits, apples, pears, avocados, etc.; nuts, such as walnuts, almonds, filberts, pecans, etc.; vegetables, such as carrots, lettuce, tomatoes, celery, turnips, potatoes, broccoli, asparagus, etc.; woody species, such as poplar, pine, sequoias, cedar, oak, etc.; ornamental flowers; or other cash crops, such as tobacco, jojoba, rapeseed, Cuphea, soybeans, sunflower, sugar beet, safflower, etc. Meristem tissue is preferred.

A wide variety of modifications may be made by using appropriate genetic constructs in combination with the implant needle array in numerous types of plants to develop transgenic varieties. These modifications may include: (1) the valuable trait of varying the fatty acid distribution of a fatty acid source, such as rapeseed, Cuphea or jojoba; (2) delaying the ripening in fruits and vegetables; (3) changing the organoleptic, storage, packaging, picking and/or processing properties of fruits and vegetables; (4) delaying the flowering or senescing of cut flowers for bouquets; (5) reducing the amount of one or more substances in the plant, such as caffeine, theophylline, nicotine; or (6) altering flower color by means of depositing genetic constructs into the cytoplasm of plant tissue using the implant needle array and subsequent selection for stable integration events.

For changing the fatty acid distribution, target species include coconut and palm trees, Cuphea species, rapeseed, or the like. The target genes of particular interest include acetyl transacylase, acetyl transferase, acyl carrier protein, thioesterase, etc.

For varying the amount of nicotine, a target species include tobacco. The target genes include N-methylputrescine oxidase or putrescine N-methyl transferase.

For delaying the ripening in fruits, the target species include tomato or avocado. The target genes include polygalacturonase or cellulase.

For varying the amount of caffeine, the target species include coffee (coffee arabica). The target genes include 7-methylxanthine, 3-methyl transferase.

For varying the amount of theophylline, the species include tea (Camellia sinensis). The target genes include 1-methylxanthine 3-methyl transferase.

For altering flower color the targets include petunia, roses, carnations, or chrysanthemums, etc. The target genes include chalcone synthase, phenylalanine ammonia lyase, or dehydrokaempferol (flavone) hydroxylases, etc.

For altering lignin content, the targets include loblolly pine, Douglas fir, poplar, alfalfa, etc. The target genes include cinnamoyl-COA:NADPH reductase or cinnamoyl alcohol dehydrogenase, etc.

Further, U.S. Pat. No. 5,107,065 is herein incorporated by reference in that it further illustrates examples for the utility of the implant needle array of the present invention and methods for production of transgenic plants which contain genetic constructs to regulate biosynthetic pathways via antisense transcripts.

BRIEF DESCRIPTION OF THE DRAWINGS

In FIG. 4A the tip portions comprise an array of sharp tips of different lengths forming a random array of biological substance receiving cavities therebetween. In FIG. 4B, the tip portions include a relatively long central or major peak surrounded by a number of side or minor peaks to define a generally circular array of cavities between the major and minor peaks.

DETAILED DESCRIPTION OF PREFERRED EMBODIMENTS OF THE INVENTION

Figure 1:
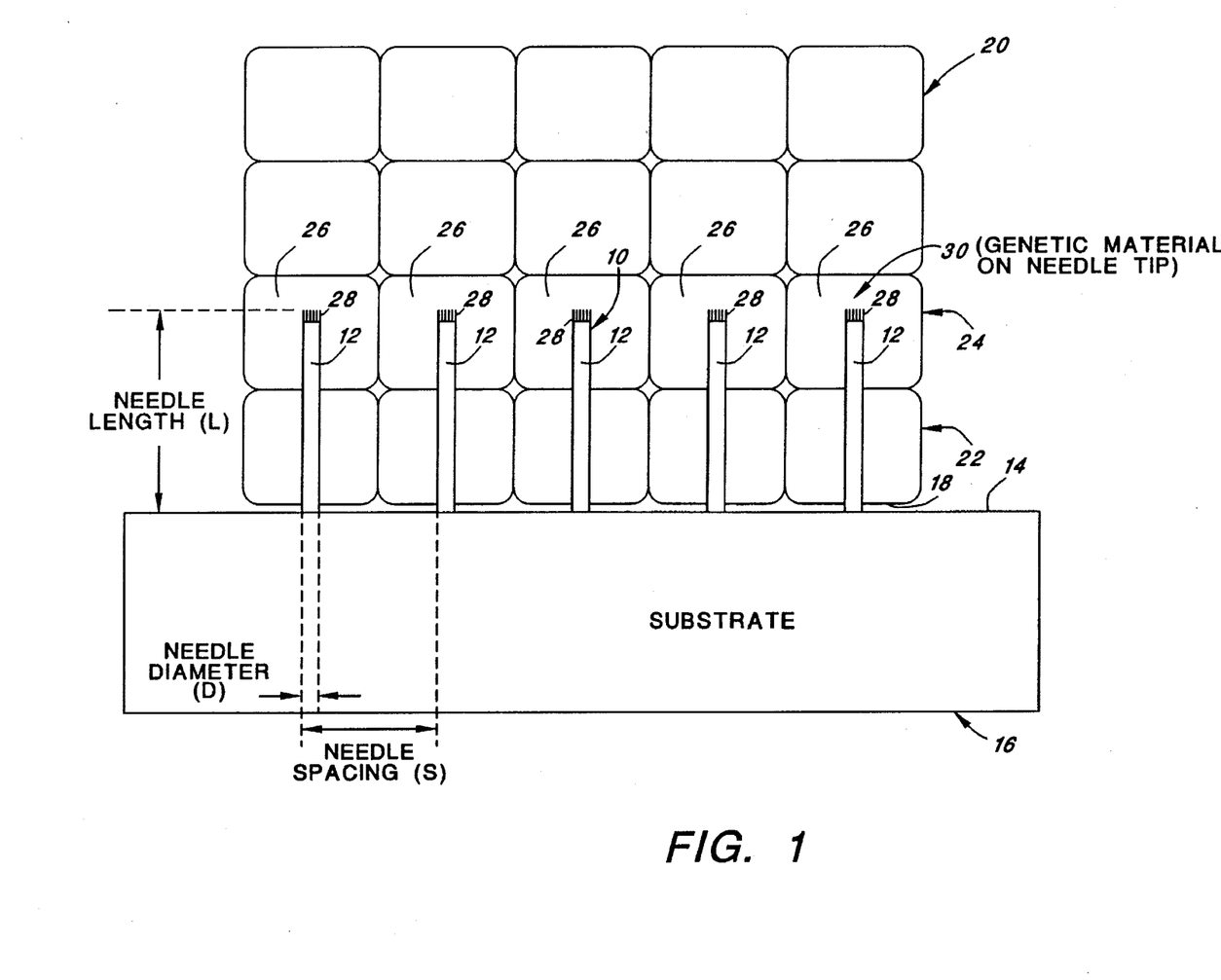
FIG. 1 is a diagrammatic representation of a basic form of the needle array of the present invention having microneedles piercing a surface of a target tissue to extend tip portions of the needles carrying a biological substance into target cells within the target tissue.

As illustrated in FIG. 1, the basic form of the apparatus of the present invention includes an array 10 of micro-needles 12 extending normal to and from a surface 14 of a support substrate or base 16. The needle length L, diameter or width D, and spacing S are depicted. In FIG. 1, the array 10 is diagrammatically represented as piercing a surface 18 of a target plant or animal tissue 20. With the surface 14 of the support substrate 16 adjacent the surface 18 of the tissue 20 the needles 12 are shown as penetrating and passing through a surface cell layer 22 to pierce and penetrate substantially midway into a target cell layer 24 comprising target cells 26. Tip portions 28 of the needles 12 are depicted as carrying a biological substance, represented generically as genetic material 30, into the target cells 26 for transfer from the tip portions and deposit into the target cells.

The needles are spaced, dimensioned and shaped to provide for effective penetration of the target tissue to the desired depth within the target cells without excessive damage to the target tissue or the target cells. In particular, the tip portions of the needles are shaped to carry biological substances for efficient transfer from the tip portions into the target cells upon penetration and withdrawal of the needles therefrom. Accordingly, as represented, the spacing S of the needles 12 preferably is equal to or slightly greater than the width of the target cells, that is, preferably between about 10 and 20 microns. Such spacing insures that excessive multiple needle penetrations of the target cells are minimized and the chances of permanent or lethal tissue damage are reduced to a minimum.

In respect to needle spacing S, while it may be preferred that the needle spacing be such that only one needle pierces a given target cell, in certain applications it may be desired that multiple needle tips pierce particular target cells. For such applications, the spacing of at least certain of the needles 12 would be less than the width of the particular target cells 26 thereby insuring that a plurality of needle tips 28 would penetrate the particular target cells and deposit the biological substance into such cells.

Further, the length L of the needles 12 preferably is greater than the thickness of the surface cells 22 plus about one-half the thickness of the target cells 26 of the target tissue 20 to insure that the tip ends 28 of the needles reach but do not extend past the target cells.

Further, the width or diameter D of the needles should be such as to allow the needles 12 to efficiently pierce the surface cell layer 22 and the target cells 26 without permanently damaging the cells of the target tissue 20. In practice, needles having a diameter of between 0.5 and 3 microns should be particularly useful in these regards.

Figure 2:
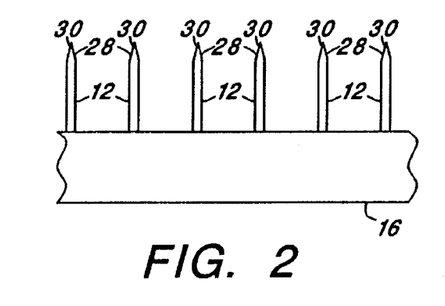
FIG. 2 is a diagrammatic side view of a section of a needle array according to the present invention where the tip portions have sharply pointed tips carrying a biological substance.
Figure 3:
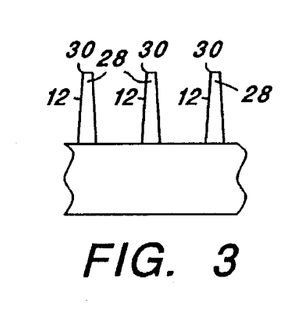
FIG. 3 is a similar side view of a section of a needle array where the tip portions have substantially flat tops.
Figure 4A:
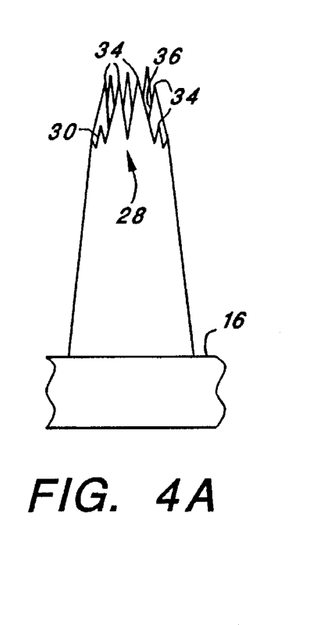
FIGS. 4A and 4B are similar side view of section of a needle array where the tip portions are ragged or cage-like including a plurality of pointed tips.
Figure 4B:
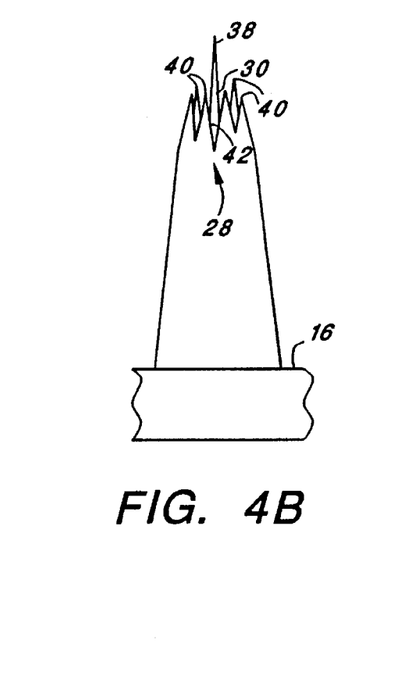
Figure 5:
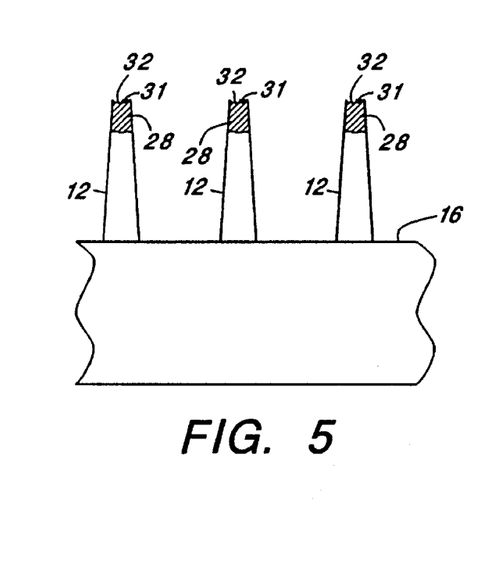
FIG. 5 is a similar side view of a section of a needle array with upper parts of the tip portions in cross-section to illustrate the concave shape of the upper surface of the tip portions.

Further, as schematically represented in FIG. 1, the biological substance comprising for example genetic material 30 is placed on the tip portions 28 of the needles 12. In this regard, the needle tips may be pointed as represented in FIG. 2, flat as represented in FIG. 3, jagged as represented in FIGS. 4A and 4B, or hollow or concave as represented in FIG. 5. The concave or jagged tips 28 afford greater efficiency of attachment of the biological substance 30 to the needles and in the case of the concave tip of FIG. 5 allows for the transfer and deposit of biological substance coated micro-particles 31 into the target cells, such particles being captured and carried within cavities 32 defined by the concave tips.

Further, with respect to the jagged tip needles of FIG. 4A, the tips comprise an array of sharp pointed peaks 34 defining cavities 36 therebetween. The pointed peaks 34 are designed to pierce the surfaces of the surface cells and the target cells while the cavities 36 are designed to carry and hold the biological substance 30 or coated micro-particles, such as 31 in FIG. 5, for the transfer of the biological substance to the target cells upon a penetration and withdrawal of the needles from the target tissue. With respect to the jagged tip needles of FIG. 4B, the needle tips comprise a sharp pointed central or major peak 38 surrounded by an annular array of smaller or minor sharp pointed peaks 40. The major peak is designed to pierce the surfaces of the surface cells and the target cells while the minor peaks are designed to hold the biological substance 30 with cavities 42 between the major and minor peaks containing the substance for transfer to the target cells upon a penetration and withdrawal of the needles from the target cells.

The biological substances 30 may be adhered to tip portions 28 and side surfaces of the needles 12 illustrated in FIGS. 2 through 5 by appropriate coating or bonding of the biological substances to the tips of the needles or by precipitation of the biological substances onto the needle tips and into the cavities of the tips of FIGS. 4A, 4B and 5 in accordance with the teachings of U.S. Pat. Nos. 5,036,006; 5,066,587; 5,100,792; 5,120,657; and 5,149,655.

Alternatively, the needles of the needle array 10 may be loaded with a biological substance by either a mechanical or an electrical approach. In the mechanical approach, the needles are pushed through a thin protective film about 12 microns thick and then painted or otherwise coated with particles of the biological substance which are then allowed to dry. The film is then removed leaving the coated particles adhering to the tips of needles of the needle array. In the electrical loading approach, the needle tips are placed in a solution of a biological substance and electrical charge applied to the needle array to attract the biological substance (etdena) to the needle points where the field is the strongest. The array of needles is then removed from the solution and allowed to dry thereby allowing the biological substance to coat the tips of the needle array.

Further along the lines of the electrical loading approach, a reversal of the electrical charge may be utilized in the application of the biological substance to the target tissue. For example, an electrical charge may be applied to the needles after they have pierced the target cells to enhance the removal of the biological substance from the needles for deposit in the target cells. Similarly, as previously discussed, when it is desired to leave the biological material coated tips of the needles in the target cells a breaking of the tip ends from base portions of the needle may be produced by the application of ultrasonic energy to, or lateral movement of, the needles.

The needle arrays may be fabricated utilizing a number of different methods. For example, the needle forming techniques described in U.S. Pat. Nos. 4,969,468 and 5,138,220 may be utilized. Preferably however, the following photolithographic etching fabrication technique has proven to be particularly useful in the production of relatively uniform needles of uniform spacing and controlled diameter, length and tip configuration. In this regard, a standard micro-circuit silicon wafer having a thickness of approximately 0.015 inches may comprise the starting material for the needle array. The silicon wafer is covered with a layer of silicon dioxide approximately 1.6 microns thick which forms the mask material for the etching process. The silicon dioxide layer is produced in a conventional manner by heating the silicon wafer in a supply of oxygen until the desired oxide thickness is achieved. Next, the coated silicon wafer is vapor primed with hexamethyl disilazane (HMDS) to provide adhesion for the subsequently applied photoresist. The photoresist is applied uniformly over the upper surface of the oxide coating on the silicon wafer to a thickness of about 1.2 microns. The wafer is then baked at about 115 degrees centigrade for one minute to fix the photoresist.

Using a conventional CAD machine, a drawing including arrays of different desired needle diameters and spacings is prepared. For example, arrays of holes having diameters of 1.2, 1,5 and 2 microns and spacings of 5, 10, 12. 15 and 20 microns may be formed on the drawing, each array comprising holes for forming a needle array of about 20 by 20 needles.

The CAD drawing is used in a conventional manner to form a mask plate. For example, the CAD drawing may be placed over a quartz plate having a chromium coating to expose the chromium with a pattern corresponding to the hole arrays on the drawing. The chromium is then etched off leaving the desired pattern on the quartz plate comprising the mask plate.

The mask plate is used in a standard photolithographic machine, such as a GCA 6300 5:1 G-Line Stepper Lithographic Machine, to expose the photoresist on the wafer with the desired hole patterns included in the mask plate. In this process, UV light is passed through the holes to the photoresist and the photoresist is then developed in a conventional developer solution. The wafer is then washed to remove the unwanted photoresist leaving a pattern of needle tip locations defined by the developed photoresist.

Following the washing of the wafer to remove the unwanted photoresist, the wafer is dried and placed in a conventional etcher-stripper machine, such as a Branson/IPC Model P2000 Etcher/Stripper, which functions to remove the remaining photoresist between the needle sites.

Following the removal of the excess photoresist, the wafer is placed in a standard ion etcher, such as a MRC Magnitron Ion Etcher Model MIE 720, which functions to remove the silicon dioxide between the needle sites. In this process and using the MRC Magnitron, the power setting may be about one kilowatt, the flow rate of $CHF_3$ about three standard cubic centimeters per minute and the duration of the process set at about 8½ minutes.

Following removal of the silicon dioxide, the wafer is again placed in the Etcher/Stripper machine and run for approximately one minute according to the machine's standard operating procedure for removing photoresist after processing to remove silicon dioxide.

The wafer with the silicon dioxide pattern of needle sites is then placed into a standard reactive ion etcher, such as a PlasmaTherm Model PK 1250 Reactive Ion Etcher. In the reactive ion etcher, the wafer is subjected to a chlorine etch which leaves the needles standing in the desired arrays with the desired diameters, lengths, spacing and tip configurations. More particularly, in the PlasmaTherm PK 1250, the first machine process is a one minute standard etch to remove moisture from the surface of the wafer followed by another standard one minute process to remove the native oxide which occurs on the silicon with exposure to air between operations. The next operation is the chlorine etch which removes the unwanted silicon from around the needles and leaves the needles standing on the wafer. In this plasma etch process, the chlorine is run at about 60 standard cubic centimeters per minute flow rate with a small amount of $BCl_3$ at about 1.6 standard cubic centimeters per minute. The pressure is maintained at about 20 millitorr with a dc bias on the plasma of approximately 300 volts and a power input to the plasma of about 100 watts. The plasma etch process is run for about 3 hours and results in needles having a length of about 15 microns. Longer processing times will result in longer needles. Following the 3 hour chlorine etch, the wafer is removed from the reactive ion etcher and rinsed with deionized water to remove any residual chlorine.

The wafer is subsequently dried leaving the needle patterns etched in the silicon. Following the drying process, the wafer is divided into the individual arrays of needles by (1) mounting the wafer in a support chuck, (2) carefully scribing the surface of the wafer in a rectilinear pattern, and (3) breaking the wafer along the scribe lines to form the individual arrays of needles having the needle patterns and spacing as indicated. Alternatively, the wafer may be cut into individual arrays by a diamond wafer saw.

Figure 6:
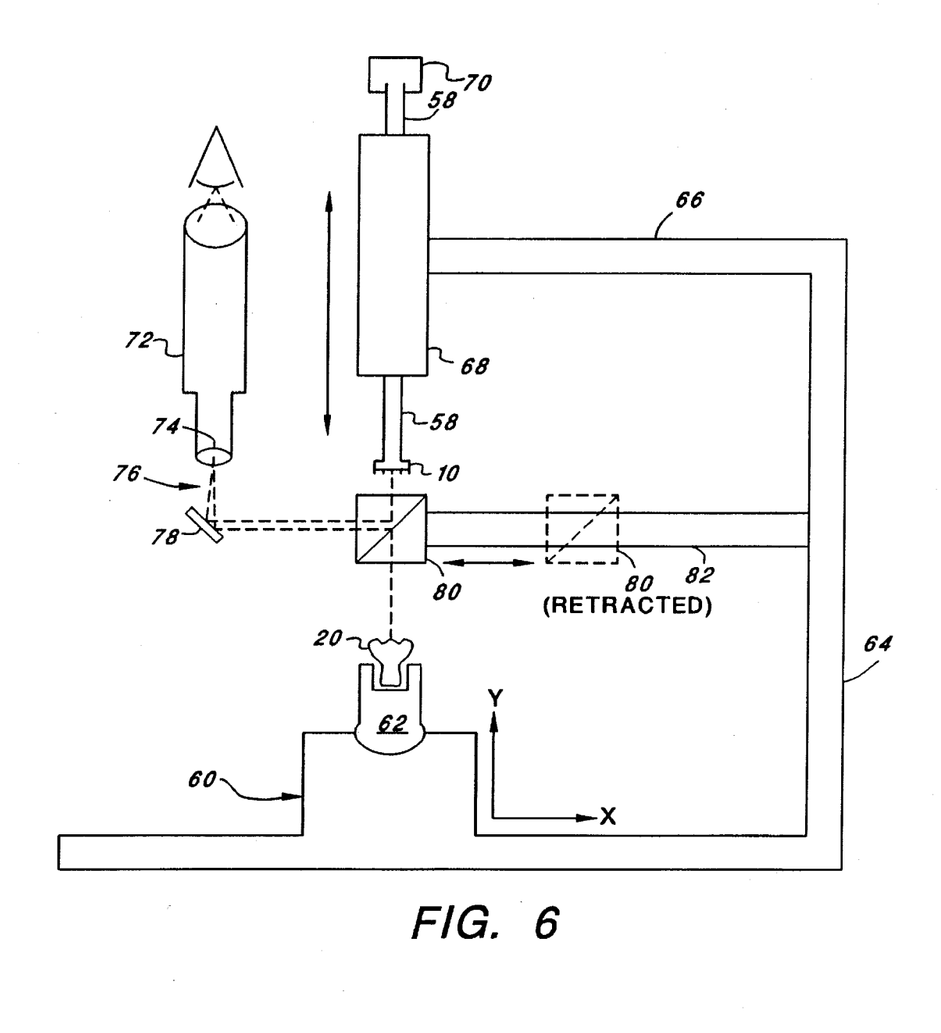
FIG. 6 is a schematic view of apparatus including a needle array for pressing the needles into a target tissue (e.g. a plant meristem) to transfer a biological substance from tip portions to target cells within the target tissue.
Figure 7:
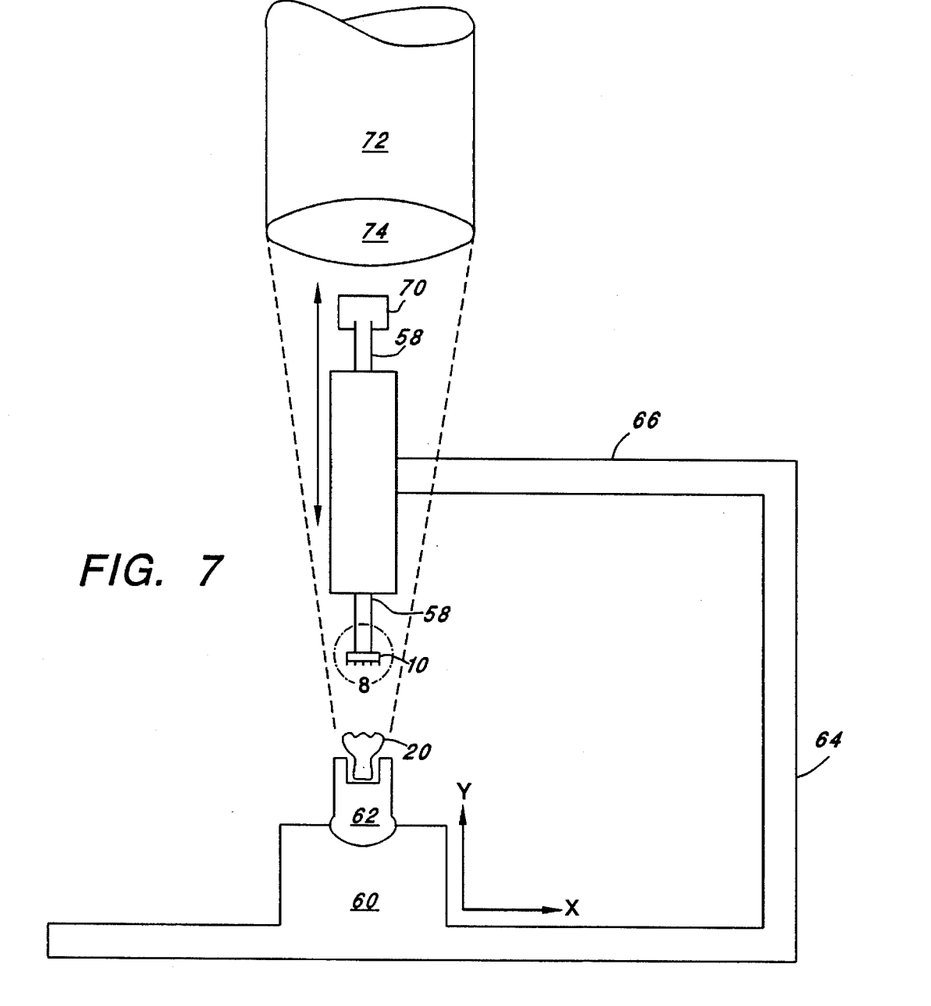
FIG. 7 is a schematic view of alternate apparatus including a needle array for pressing needles into a target tissue to transfer a biological substance from the needles into target cells within the target tissue.
Figure 8:
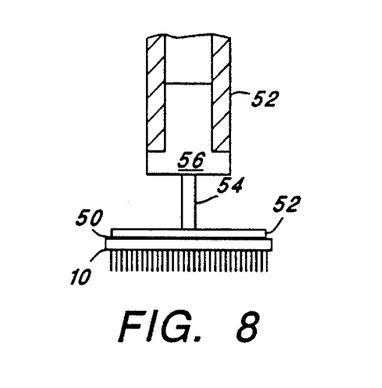
FIG. 8 is an enlarged side view, partially in section, of an end portion of a slide for carrying and moving a needle array to pierce a target tissue according to the method of the present invention.

As shown in FIG. 8, each array 10 is then mounted, as by an epoxy glue 50, to the flat end 52 of a post member 54. An opposite end 56 of the post member 54 is adapted to nest into the tubular end of a hollow cylindrical needle array holder or slide 58 in an apparatus as shown in FIGS. 6 and 7. In such a mounting arrangement, the needle supporting posts 54 may be manually gripped, as by tweezers, and transported from a support container which vertically supports the posts in a spaced array, to the cylindrical slide 58 of the FIG. 6 or 7 apparatus.

As shown in FIG. 6, the apparatus comprises a base support 60. The base 60 is moveable in X and Y directions and supports a holder 62 for securing the target tissue 20, such as a meristem of a plant. Extending vertically from the base support 60 is a vertical support member 64 for a horizontal support member 66 carrying a vertical tubular holder 68. The cylindrical slide member 58 is mounted in the holder 68 and is moveable vertically therein. The upper end of the slide 58 supports a weight or other suitable mechanism 70 for imparting selectively controlled vertical force to the slide to drive the needle array 10 into and out of the target tissue 20. In this regard, the lower end of the slide 58 supports the needle array 10 as shown in FIG. 8.

Located to a side of the holder is a microscope 72 including a viewing lens system 74 comprising part of an optic system 76 for the apparatus. In addition to the viewing lens 74, the optic system 76 includes a planar surface mirror 78 under the viewing lens and a beam splitter cube 80 carried by a horizontally retractable arm 82 extending laterally from the vertical support member 64. The microscope 72 and optic system 76 allow an operator looking into the microscope to simultaneously view the needle array 10 and the target tissue 20 and while so doing adjust the base member 60 to bring the target tissue into vertical alignment with the needle array. Once the tissue 20 is so aligned, the operator retracts the beam splitter cube 80 and releases the slide 58 allowing the weight 70 to move the slide and needle array 10 downward until the needle tips engage and pierce the surface of the target tissue. Continued downward movement of the needle array 10 then causes the needle tips to pierce the target cells and to deposit the biological substance carried thereby into the target cells upon a withdrawal of the needles by an upward movement of the slide.

An alternate apparatus for inserting biological substances into a target tissue is shown in FIG. 7 and comprises apparatus similar to FIG. 6 except that the viewing lens system of the microscope 72 is enlarged and placed directly over the slide 58 and needle array 10. Thus arranged, an operator looking into the microscope simultaneously sees the needle array 10 and the target tissue 20. Again, by controlled movement of the support base 60, the operator is then able to adjust the position of the target tissue to vertically align it with the needle array thereby readying the apparatus for insertion of the biological substance into the target cells of the tissue as previously described.

Figure 9A:
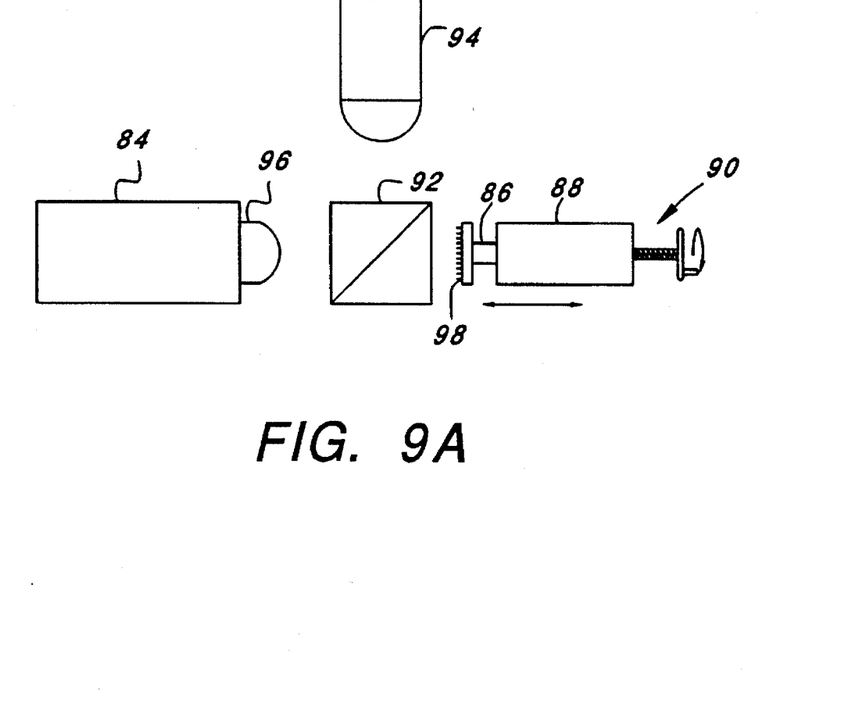
FIG. 9A is a schematic side view of a preferred apparatus including a needle array for pressing needles into a target tissue to transfer a biological substance from the needles to target cells within the target tissue.
Figure 9B:
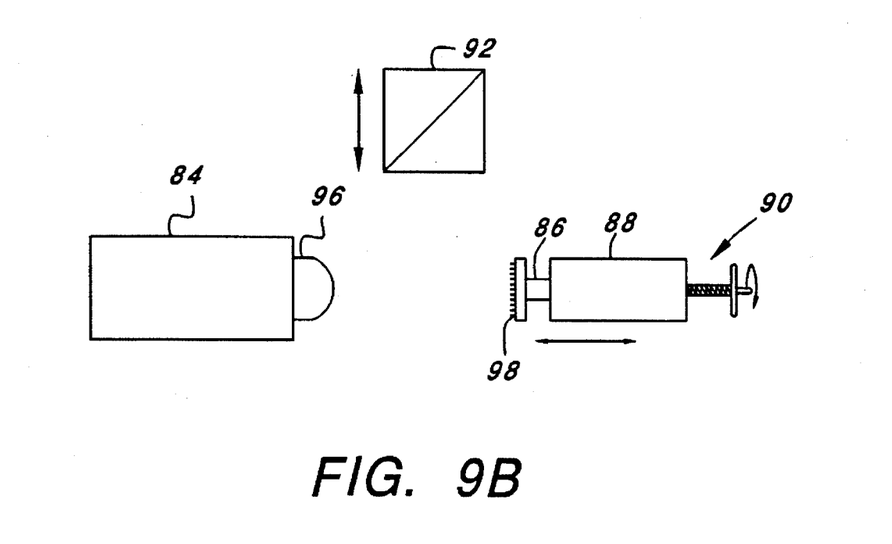
FIG. 9B is a schematic top view of the apparatus of FIG. 9A.

A currently preferred apparatus for inserting biological substances into target tissue is shown schematically in FIGS. 9a and 9b. The apparatus resembles that of FIG. 6 except that it is designed to horizontally support and move the needle array into the target tissue. In this regard, the apparatus comprises a target tissue holder 84, a needle array carrying slide member 86, a slide support 88, a slide mover 90, a beam splitter 92 and a microscope 94. The holder 84, slide member 86, slide support 88, beam splitter 92 and microscope 94 may be the same as or substantially similar to corresponding components shown and previously described with reference to FIGS. 6, 7, and 8. The holder 84, slide 86, support 88 and beam splitter 92 are mounted on a common base (not shown) such that the holder and slide are aligned in a common horizontal plane and are manually moveable axially toward and away from each other. The beam splitter 92 is mounted by support structure (not shown) to be manually moveable in a direction normal to the horizontal plane of the holder and slide to bring the beam splitter into and out of alignment with the axis of the holder and slide. The microscope 94 is removably mounted above the base over the beam splitter 92 when it is aligned with the holder and slide. In this manner, with a target tissue 96 secured to the holder 84 and facing the needle array 98 carried by the slide 86, and with the microscope 94 over the beam splitter 92, an operator is able to simultaneously view the target tissue and the needle array and to adjust the positions thereof until the target and array are in horizontal and axial alignment. The operator can then retract the beam splitter 92 and relocate the microscope 94 over the target tissue 96. Finally, by operating the slide mover 90 (e.g. a conventional feed screw drive, the operator can drive the needle array 98 into and out of the target tissue 96 to effect a transfer of biological substance from the needles to target cells within the target tissue.

While particular preferred embodiments of the needle arrays and apparatus for inserting biological substances into target tissues using the needle arrays have been described in detail above, changes in the illustrated embodiments may be made without departing from the spirit of the present invention. Accordingly, it is intended that the present invention be limited in scope only by the terms of the following claims.

We claim:

1. Apparatus for depositing biological substances into target cells in living plant or animal target tissue, the apparatus comprising:

a mechanical holder for securing a target tissue;

a target tissue secured by the holder and including target cells having a known width and depth from a surface of the target tissue;

an array of micro-needles substantially normal to and extending from a surface of a support substrate for piercing the surface of the target tissue to penetrate the target cells, the needles having a length greater than the depth of the target cells and sufficient to pierce the target cells when the needles are forced into the tissue with the surface of the support substrate adjacent to the surface of the tissue, and a spacing substantially equal to the width of the target cells which allows each needle to pierce one of the target cells, at least a portion of each needle carrying a biological substance for transfer to and deposit within the target cells upon a piercing thereof by the needles;

means for supporting the array of micro-needles relative to the holder; and means for moving the array of micro-needles relative to the holder to penetrate the target tissue until the surface of the support substrate is adjacent the surface of the target tissue.

2. The apparatus of claim 1 wherein the needles have a base width at the surface of the support substrate of between about 0.5 and 3 microns.

3. The apparatus of claim 2 wherein the length of the needles is between about 10 and 25 microns.

4. The apparatus of claim 3 wherein the spacing of the needles is between about 5 and about 20 microns.

5. The apparatus of claim 4 wherein the needle array has a size up to about 20 needles by 20 needles.

6. The apparatus of claim 1 wherein the needles include tip portions at least some of which are pointed.

7. The apparatus of claim 1 wherein the needles include tip portions at least some which are concave to define a biological substance receiving cavities.

8. The apparatus of claim 7 wherein the biological substance is carried by micro-particles in the cavities.

9. The apparatus of claim 1 wherein the needles include tip portions at least some of which include a major pointed tissue piercing peak surrounded by minor pointed peaks for carrying the biological substance in cavities between the major and minor peaks.

10. The apparatus of claim 1 wherein the needles include tip portions at least some of which are of a ragged, cage-like construction including a plurality of pointed peaks having biological substance receiving cavities therebetween.

11. The apparatus of claim 1 wherein;

the mechanical holder is movable in X and Y directions relative to the means for supporting the array of micro-needles, and the means for supporting the array of micro-needles comprises a tubular holder, a movable slide in the tubular holder, and means for securing the array of micro-needles at one end of the slide to move relative to the target tissue on the mechanical holder.

12. The apparatus of claim 11 further including means at an opposite end of the slide for moving the slide and array of micro-needles to pierce the target tissue.

13. The apparatus of claim 11 further including a microscope for simultaneously viewing the array of micro-needles and the target tissue to allow for controlled X and Y movement of the mechanical holder relative to the tubular holder to align the target tissue and the array of micro-needles.

14. The apparatus of claim 13 wherein:

The microscope including a viewing lens is spaced from the target tissue and array of micro-needles, and the apparatus further comprises an optics system including beam splitter means between the array of micro-needles and the target tissue for simultaneously reflecting images of the array of micro-needles and the target tissue to the microscope for simultaneous viewing by an operator wherein the beam splitter means is mounted for movement from the optic system after the array of micro-needles and target tissue have been aligned.

15. The apparatus of claim 13 wherein the microscope includes an object viewing lens aligned with the array of micro-needles and target tissue for a simultaneous viewing thereof.

16. A method of depositing a biological substance into target cells in a living plant or animal tissue, the target cells having a known width and depth from a surface of the target tissue, the method comprising the step of:

(a) securing the tissue on a base;

(b) mounting an array of micro-needles having tip portions carrying the biological substance or biological substance carrying micro-particles to a holder and aligning the array of needles with the tissue on the base, the needles having a length greater than the depth of the target cells and sufficient to pierce the target cells when the needles are forced into the tissue with the surface of a support substrate for the micro-needles adjacent to the surface of the tissue, and a spacing substantially equal to the width of the target cells to allow each needle to pierce one of the target cells;

(c) moving the holder relative to the tissue to force the array of needles into the tissue until the tip portions penetrate the target cells to allow the biological substance to transfer into the target cells; and (d) withdrawing the needle away from the tissue.

17. The method of claim 16 wherein aligning the array of needles and the tissue comprises simultaneously viewing the array and tissue with a microscope and while so viewing, moving the base relative to the holder until the array and tissue are aligned.

18. The method of claim 16 further comprising breaking off tip portions of the needles carrying the biological substance within the target cell to remain therein upon the withdrawing of the needles from the tissue.

* * * * *